United States Patent [19]

Andersen et al.

[11] Patent Number: 4,950,254

[45] Date of Patent: Aug. 21, 1990

[54] VALVE MEANS FOR ENTERAL THERAPY ADMINISTRATION SET

[75] Inventors: Erik Andersen, Vernon Hills; Charles Dillon, Lincolnshire, both of Ill.

[73] Assignee: Corpak, Inc., Wheeling, Ill.

[21] Appl. No.: 257,726

[22] Filed: Oct. 14, 1988

[51] Int. Cl.$^{5}$ .............................................. A61M 31/00

[52] U.S. Cl. .................................... 604/247; 604/256; 604/905; 604/213

[58] Field of Search ............... 604/246, 247, 256, 257, 604/905, 213, 151, 153

[56] References Cited

U.S. PATENT DOCUMENTS

| | | | |
|---|---|---|---|
| 1,903,681 | 4/1933 | Merliss | 604/213 |
| 3,664,339 | 5/1972 | Santomieri | 604/213 |
| 4,259,952 | 4/1981 | Avoy | 604/213 |
| 4,354,492 | 10/1982 | McPhee | 604/247 |
| 4,405,316 | 9/1983 | Mittleman | 604/247 |
| 4,685,912 | 8/1987 | Jones | 604/247 |
| 4,735,607 | 4/1988 | Keith, Jr. | 604/247 |

*Primary Examiner*—C. Fred Rosenbaum
*Assistant Examiner*—Denise W. DeFranco
*Attorney, Agent, or Firm*—Wallenstein, Wagner & Hattis, Ltd.

[57] ABSTRACT

A one way valve means for incorporation into a fluid administration set for enteral therapy which arrests retrograde movement of fluid into the set to avoid flow rate interruption or, in the event of extreme fluid back pressure, rupturing of the tubing in the set. The one way valve means is responsive to fluid back pressure and is incorporated in a male connector disposed on a distal end of the administration set tubing. As a result retrograde fluid movement caused by either irrigation or patient originated, fluid back pressure is immediately arrested before fluid enters the administration set.

2 Claims, 1 Drawing Sheet

VALVE MEANS FOR ENTERAL THERAPY ADMINISTRATION SET

DESCRIPTION

1. Technical Field

The present invention generally relates to the field of enteral therapy, and, in particular, to a one way valve means for preventing fluid backflow or retrograde fluid movement through an enteral fluid administration set.

2. Background Art

Enteral therapy is achieved through intubation of a nasogastric feeding tube. Typically, the feeding tube is joined at a proximal end to a container, which provides a source of nutritional solution. Interposed between the proximal end of the feeding tube and the container is a fluid administration set. For gravity feeding of enteral solutions the set typically comprises a segment of tubing linking the feeding tube with the container. Usually the tubing segment has an inner diameter larger than the inner diameter of the feeding tube. In addition, the tubing segment includes a male connector on a distal end for seating in a female connector disposed on the proximal end of the feeding tube. A tube clamp for regulating fluid flow may also be interposed along the tubing segment. A drip chamber may also be carried on the tubing segment near the container. The drip chamber may also include a hollow spike for connecting to the container of enteral nutritional solution.

Where pumping of enteral fluid is desired a pump administration set is connected to the proximal end of the feeding tube. A pump administration set comprises essentially the same elements of a gravity feeding set except that a pump set also includes a portion of specially selected tubing, often made from silicone, which is interposed along the tubing segment. This portion of silicone tubing is wrapped around the rotor of a peristaltic pump and is sequentially occluded by the rotor to achieve a pumping action.

To irrigate, aspirate or administer oral medications through a nasogastric enteral feeding tube, a "Y" connector may be inserted between the proximal end of the feeding tube and the male connector of the administration set. More recently, Y connectors have been integrally formed on the proximal end of the feeding tubes to eliminate the need for separate Y connector sets. By using a Y connector, the feeding tube can be irrigated, aspirated or injected with medication without disconnecting the feeding tube from the administration set. A side arm of the Y connector receives a luer tip syringe or may be adapted to receive a cath tip syringe.

A problem with Y connectors is that if the feeding tube is occluded, the pressure of irrigating fluid, for example, is directed in a retrograde direction into the administration set. Prior to Y connectors, this pressure was released when the feeding tube was disconnected from the administration set. The fluid pressure created by a 50–60 ml. irrigating syringe can exceed 20–30 psi. In the case of pump administration sets, the fluid pressure travels through the set until it meets the resistance of the occluded tubing wound around the pump rotor and bursts the tubing. To avoid this costly result, which requires replacement of the fluid administration set and an interruption in patient therapy, a pinch clamp may be used distal to the connection of the administration set with the feeding tube. In the alternative, the user may pinch the tubing at this same point. However, if the user neglects to do this or the pinch clamp fails, then rupture of the administration set will likely result during irrigation or medication administration.

In addition to retrograde fluid movement created by irrigation backflow, it has been observed that retrograde movement of fluid within the feeding tube and into the administration set also results when an intubated patient moves, coughs, laughs or belches. That is, the source of fluid back pressure within the administration set is the patient himself. Such patient-originated retrograde fluid movement disrupts accurate fluid flow rate which is important to effective enteral therapy.

Hence, prior to the development of the present invention a need existed for a one way valve means to be incorporated preferably into a distal segment of a fluid administration set which would respond to fluid backflow pressure and automatically arrest retrograde movement into the tubing of an administration set.

SUMMARY OF THE INVENTION

According to the present invention, a one way valve means for incorporation into a fluid administration set for enteral therapy has been developed which responds to fluid backflow pressure and arrests retrograde movement of fluid into the set thereby avoiding any rupturing of the tubing in the set. In the broader aspects of the present invention, the one way valve means may be interposed in a pump administration set anywhere between the portion of administration set tubing which is wound around the rotor of a peristaltic pump and the proximal end of the feeding tube. In a gravity fed administration set the one way valve means may be interposed anywhere along the tubing distal to the clamp which regulates fluid flow. In the preferred embodiment of the present invention, the one way valve means is incorporated in a male, luer type connector disposed on a proximal end of the administration set tubing. As a result, retrograde fluid movement caused by either irrigation or patient-originated fluid back pressure is immediately arrested before fluid enters the administration set.

Broadly, the one way valve means of the present invention may embody duck bill valves, ball check valves, flap valves or any one way valve known in the medical fluid administration art which responds to a selected level of fluid pressure. In the preferred embodiment of the present invention, a ball check valve is carried within the male luer type connector near the distal end of the tubing segment. Hence, any significant fluid backflow pressure causes the ball to seat to prevent any fluid flow into the administration set.

Other advantages and aspects of the invention will become apparent upon making reference to the specification, claims, and drawings to follow.

DETAILED DESCRIPTION

Figure 1:
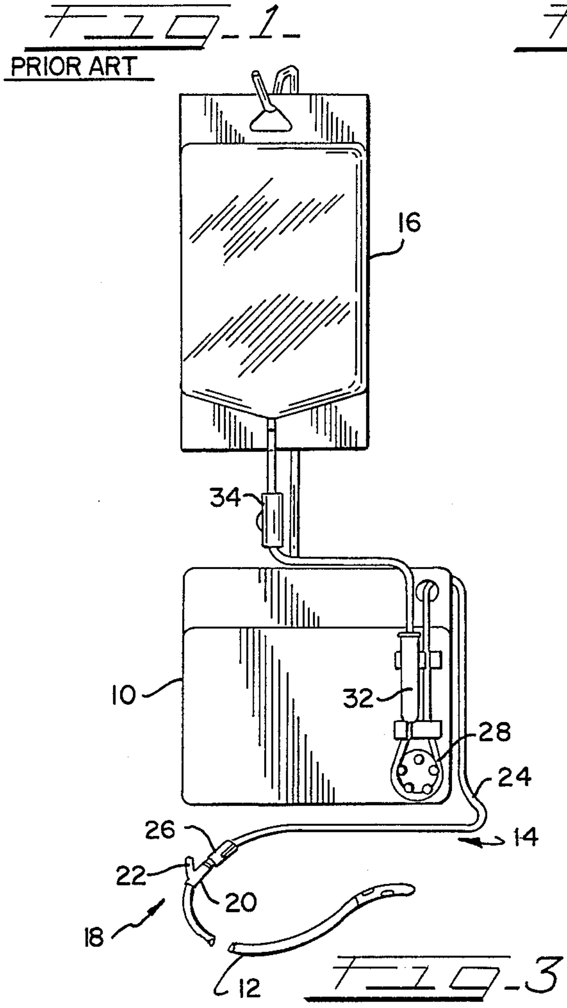
FIG-1- PRIOR ART
FIG. 1 discloses in a perspective view a prior art pump driven enteral administration set.

While this invention is susceptible of embodiment in many different forms, there is shown in the drawings and will be described in detail a preferred embodiment of the invention. The present disclosure is to be considered only as an exemplification of the principles of the invention and is not intended to limit the broad aspect of the invention to embodiment illustrated.

Referring now to the drawings, FIG. 1 discloses enteral therapy fluid delivery system utilizing a peristaltic pump 10, a nasogastric feeding tube 12, a pump administration set generally referenced by 14 and a container 16 providing a source of therapeutic fluid. Feeding tube 12 carries a Y connector 18 on a distal end of the tube. Connector 18 includes a primary arm 20 and a side arm 22. Primary arm 20 embodies a female connector to join feeding tube 12 to pump administration set 14. Side arm 22 may receive a syringe tip for aspirating, irrigating or administering oral medications into feeding tube 12.

Pump set 14 is exemplary of prior art pump sets and includes a segment of tubing 24 which generally has an inner and outer diameter larger than feeding tube 12. Disposed on a distal end of tubing segment 24 is a male connector 26 which seats within the primary arm 20 of feeding tube 12. As will be explained later in greater detail, in the preferred embodiment of the present invention, male connector 26 carries a one way valve means responsive to fluid back pressure to arrest retrograde fluid movement from feeding tube 12 through tubing segment 24.

Distal to male connector 26, pump set 14 also includes a separate portion of tubing spliced in tubing segment 24 which functions as a pump body 28. As disclosed in FIG. 1, pump body 28 is stretched and wound around a rotor 30 of pump 10 to thereby sequentially compress pump body 28 to generate a peristaltic pumping action. For durability, pump body 28 is formed from silicone.

Immediately distal to pump body 28 is a drip chamber 32 which acts to evenly deliver fluid in the pump body 28. Finally, near the distal end of the tubing segment 24 is a clamp 34 for regulating fluid flow to drip chamber 32.

Figure 2:
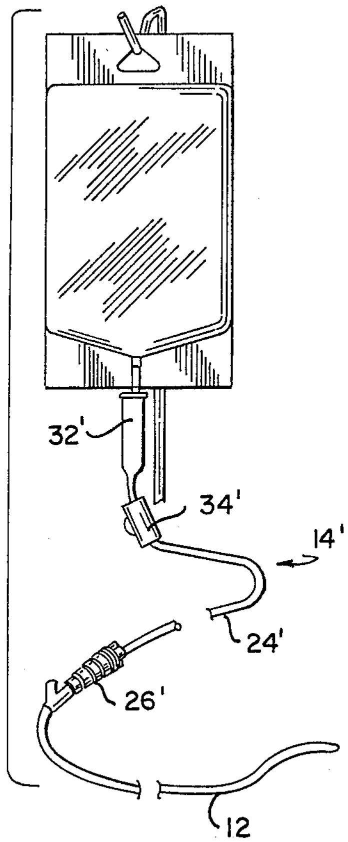
FIG. 2 discloses in a perspective view the one way valve means of the present invention embodied in a gravity fed enteral administration set.

FIG. 2 discloses an administration set 14' which is utilized for gravity fed enteral therapy. Set 14' includes a segment of tubing 24' on a distal end of which is a male connector 26'. In a preferred embodiment of the present invention, male connector 26' carries a one way valve means responsive to fluid back pressure to arrest retrograde fluid movement from feeding tube 12 through tubing segment 24'.

In gravity administration set 14', tubing segment 24' does not include a pump body 28. As a result, a drip chamber 32' is positioned at the proximal end of tubing segment 24'. Near drip chamber 32' is a clamp 34'.

To irrigate, aspirate or administer oral medications through feeding tube 12, a syringe tip may be inserted into side arm 22 carried on the proximal end of feeding tube 12. However, if feeding tube 12 is occluded or a syringe of an improper size is selected, fluid back pressure results in feeding tube 12 and travel through tubing segment 24 of, for example, pump administration set 14. Typically, such fluid back pressure will continue to move in a retrograde direction through tubing segment 24 until reaching the portion of tubing segment 24 which carries pump body 28. Typically, the fluid back pressure ruptures the splice of pump body 28 with tubing segment 24. At a minimum, the administration set must be replaced and, as disclosed in FIG. 1, where the container 16 is permanently affixed to administration set 14, it is also necessary to replace the container.

Retrograde fluid movement from the feeding tube into the tubing segment 24 of an administration set has been observed to result when an intubated patient moves, coughs, laughs or belches. While patient originating fluid back pressure may not burst or rupture any portion of the tubing segment of the administration set, such retrograde fluid movement disrupts accurate fluid flow rates which are important to effective enteral therapy.

Figure 3:
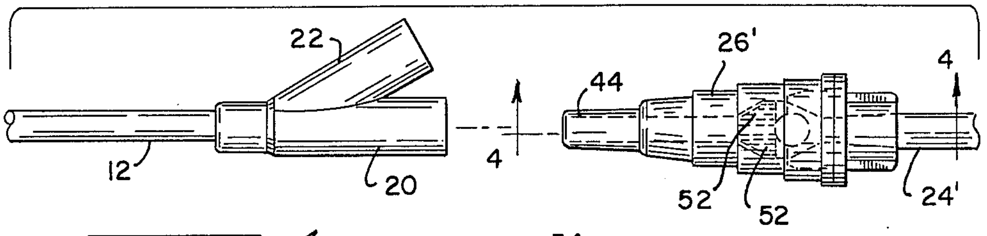
FIG. 3 discloses the one way valve means of the present invention preferably embodied in a male luer type connector; and, FIG. 4 is a sectional view of the connector disclosed in FIG. 3.
Figure 4:
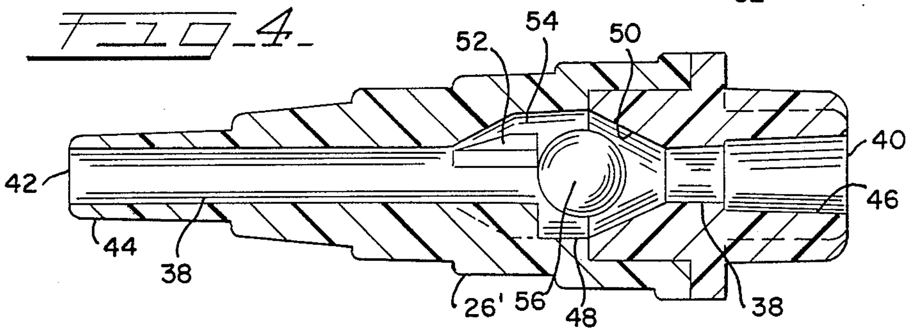

Hence, in the preferred embodiments of the present invention, a one way valve means responsive to fluid back pressures may be incorporated within the male connector 26 of pump set 14 or male connector 26' of gravity set 14'. Although such one way valve means may embody duckbill valves, flap valves or other one way check valves, preferably a ball check valve may be embodied within male connector 26. As best disclosed in FIGS. 3 and 4, connector 26' has an internal axial bore 38 which joins a fluid inlet 40 on one end of connector 26 with a fluid outlet 42 on an other end of connector 26'. In normal operation, fluid flows from tubing segment 24' and enters connector 26' at fluid inlet 40, passes through axial bore 38 and exits connector 26' at fluid outlet 42. Connector 26' is provided with a luer type fitting 44 so as to seat within primary arm 20 on feeding tube 12. Fluid inlet 40 is provided with a recessed cavity 46 for receiving the distal end of tubing segment 24'.

The one way ball check valve mechanism of connector 26 includes a valve chamber 48 which generally has inner dimensions larger than the inner diameter of bore 38. One side of chamber 48 which is directed to fluid inlet 40 defines a valve seat 50. Likewise, an other side of chamber 48 which is directed to fluid outlet 42 carries a plurality of fingers 52 which project from side walls 54 of chamber 48 which fingers 52 function as a valve stop.

Finally, the ball check valve mechanism of the present invention includes a generally spherical valve member 56 which may freely float about chamber 48. However, movement of valve member 56 within chamber 48 is limited in the direction of fluid outlet 42 by valve stops 52 and is likewise limited in the direction of fluid inlet 40 by valve seat 50. In response to fluid back pressure flowing into fluid outlet 42 and in the direction of fluid inlet 40 urges valve member 56 to move within chamber 48 in the direction of fluid outlet 40. If fluid back pressure is sufficient, then valve member 56 is forced to abut against valve seat 50, thereby sealing any fluid access to fluid inlet 40 to automatically arrest retrograde fluid movement into tubing segment 24. It should be understood that valve member 56 could be replaced with a flap or by valve, duckbill type arrangement which would likewise respond to sufficient fluid back pressure to seal any fluid access to fluid inlet 40 thereby arresting retrograde fluid movement.

While the specific embodiments have been illustrated and described, numerous modifications come to mind without significantly departing from the spirit of the invention and the scope of protection is only limited by the scope of the accompanying claims.

We claim:

1. In a pump administration set for enteral feeding of therapeutic fluids, the set including at least a tubing segment connecting a source of therapeutic fluids with a nasogastric feeding tube, the tubing segment having a portion being compressible by a peristaltic pump, and a male connector on a distal end of the tubing segment for coupling with a female connector on a proximal end of the nasogastric feeding tube, the improvement to the set comprising:

one way valve means carried within the male connector, the valve means being responsive to fluid backflow pressure to arrest retrograde fluid movement from the feeding tube through the tubing segment of the administration set;

the one way valve means including a valve housing interposed along the tubing segment, the housing having a fluid inlet on one end joined to the tubing segment to receive fluid from the source and a fluid outlet on an other end joined to the tubing segment to transmit fluid to the feeding tube, the housing having an internal axial bore connecting the fluid inlet with the fluid outlet;

a valve chamber positioned along and coaxial with the bore, one side of the chamber opening to the fluid inlet and defining a valve seat thereon, an other side of the chamber opening to the fluid outlet; and, a valve member disposed within the valve chamber, the valve member being movably responsive to fluid pressure from the fluid outlet;

such that the valve member is urged against the valve seat by the fluid pressure thereby preventing fluid access to the fluid inlet and to arrest retrograde movement of fluid within the tubing segment.

2. The pump administration set for enteral feeding of therapeutic fluids described in claim 1 wherein the valve means includes a ball check valve.

* * * * *